United States Patent
Bostick et al.

(10) Patent No.: US 9,633,019 B2
(45) Date of Patent: Apr. 25, 2017

(54) AUGMENTING AN INFORMATION REQUEST

(71) Applicant: INTERNATIONAL BUSINESS MACHINES CORPORATION, Armonk, NY (US)

(72) Inventors: James E. Bostick, Cedar Park, TX (US); John M. Ganci, Jr., Cary, NC (US); Sarbajit K. Rakshit, Kolkata (IN); Craig M. Trim, Sylmar, CA (US)

(73) Assignee: International Business Machines Corporation, Armonk, NY (US)

( * ) Notice: Subject to any disclaimer, the term of this patent is extended or adjusted under 35 U.S.C. 154(b) by 286 days.

(21) Appl. No.: 14/589,110

(22) Filed: Jan. 5, 2015

(65) Prior Publication Data

US 2016/0196264 A1 Jul. 7, 2016

(51) Int. Cl.
*G06F 17/30* (2006.01)
*G06F 7/00* (2006.01)
*H04N 5/232* (2006.01)
*G06F 19/00* (2011.01)

(52) U.S. Cl.
CPC .. *G06F 17/30038* (2013.01); *G06F 17/30026* (2013.01); *G06F 17/30268* (2013.01); *G06F 19/703* (2013.01); *H04N 5/23222* (2013.01)

(58) Field of Classification Search
USPC ........................................................ 707/706
See application file for complete search history.

(56) References Cited

U.S. PATENT DOCUMENTS

| | | |
|---|---|---|
| 8,503,787 B2 | 8/2013 | Boncyk et al. |
| 8,818,986 B1 | 8/2014 | Delker et al. |
| 2008/0005091 A1 | 1/2008 | Lawler et al. |
| 2009/0150156 A1 | 6/2009 | Kennewick et al. |
| 2012/0016678 A1 | 1/2012 | Gruber et al. |
| 2012/0078889 A1 | 3/2012 | Chu-Carroll et al. |
| 2012/0124461 A1 | 5/2012 | Barnett et al. |
| 2012/0166202 A1 | 6/2012 | Carriere et al. |
| 2012/0239401 A1 | 9/2012 | Arakawa |
| 2013/0044042 A1 | 2/2013 | Olsson et al. |
| 2013/0086105 A1 | 4/2013 | Hammontree et al. |

(Continued)

FOREIGN PATENT DOCUMENTS

| | | |
|---|---|---|
| CN | 101479728 A | 7/2009 |
| CN | 103229120 A | 7/2013 |

(Continued)

OTHER PUBLICATIONS

Anonymous, "Baidu Once, You Really Know?" PC Fan 31, Dec. 2009, pp. 1-2 (No Translation Available).

(Continued)

*Primary Examiner* — Kuen Lu
(74) *Attorney, Agent, or Firm* — Law Office of Jim Boice

(57) ABSTRACT

An electronic device comprises a microphone for receiving an oral request for information about an unspecified object. A sensor receives augmentation information about the unspecified object. Combination logic combines information from the oral request with the augmentation information into a combined format information request. Information retrieval logic then retrieves an answer to the combined format information request.

8 Claims, 5 Drawing Sheets

(56) References Cited

U.S. PATENT DOCUMENTS

| | | | |
|---|---|---|---|
| 2013/0114849 A1 | 5/2013 | Pengelly et al. | |
| 2013/0185068 A1 | 7/2013 | Tanaka et al. | |
| 2013/0249948 A1* | 9/2013 | Reitan | G06F 3/011 345/633 |
| 2013/0346068 A1 | 12/2013 | Solem et al. | |
| 2014/0370841 A1 | 12/2014 | Roberts et al. | |
| 2015/0256891 A1* | 9/2015 | Kim | H04N 5/602 725/39 |
| 2015/0379042 A1* | 12/2015 | Schupp | G06K 9/62 707/722 |

FOREIGN PATENT DOCUMENTS

| | | |
|---|---|---|
| CN | 104239445 A | 12/2014 |
| CN | 104239461 A | 12/2014 |

OTHER PUBLICATIONS

International Application No. PCT/IB2015/060046, International Searching Authority, International Search Report and Written Opinion Mailed May 4, 2016.

Apple, Inc. "Apple—iOS 8—Siri", Apple, Inc., www.apple.com, retrieved Oct. 18, 2014, pp. 1-3.

C. Kotapuri et al., "Image Search Engine Based on Combined Features of Image Sub-Blocks", International Journal of Image Processing and Vision Sciences ISSN, vol. 1, No. 2, 2012, pp. 10-16.

S. Tsai et al., "Combining Image and Text Features: A Hybrid Approach to Mobile Book Spine Recognition", ACM, MM'11, 2011, pp. 1-4.

Anonymous, "Image Recognition and Web Search", Networks, Course Blog for INFO 2040/Econ 2040/SOC 2090, Cornell University, Nov. 9, 2011, pp. 1-2.

Anonymous, "New Apps Use Image Recognition to Identify Products", Reuters, The Business of Fashion, Aug. 26, 2013, pp. 1-2.

D. Oran, "Requirements for Distributed Control of Automatic Speech Recognition (ASR), Speaker Identification/Speaker Verification (SI/SV), and Text-to-Speech (TTS) Resources (RFC4313)", IP.com, IPCOM000132358, The Internet Society, Dec. 2005, pp. 1-22.

Z. Han et al., "Robust Voice Activity Detection Based on the Static and Dynamic Energy for the Embedded System", IP.com, IPCOM000125925, Motorola, Inc., Jun. 22, 2005, pp. 1-5.

J. Clover, "Siri Photo Search System Detailed in New Apple Patent", MacRumors.com LLC, macrumors.com, Dec. 26, 2013, pp. 1-8.

Google, "Search by Image", Google, Inc., www.google.com, retrieved Sep. 12, 2014, pp. 1-3.

P. Parker, "Google Voice Search & Search by Image Comes to Desktops", Third Door Media, Inc., Search Engine Land, www.searchengineland.com, Jun. 14, 2011, pp. 1-5.

P. Mell et al., "The NIST Definition of Cloud Computing", National Institute of Standards and Technology, Information Technology Laboratory, Special Publication 800-145, Sep. 2011, pp. 1-7.

* cited by examiner

AUGMENTING AN INFORMATION REQUEST

BACKGROUND

The present disclosure relates to the field of information retrieval, and specifically to the field of information retrieval based on a query by a user. Still more specifically, the present disclosure relates to the field of interpreting user-generated queries.

Many mobile devices today have the capability of receiving an oral question from a user, and then responding with an answer using speech synthesis.

For example, U.S. Patent Application Publication No. 2012/0016678 describes an intelligent automated assistant that engages with a user using a natural language dialog in order to answer specific questions from the user. However, such systems are limited to speech inputs from the user, which can result in erroneous responses by the mobile device. For example, a user may ask a question that is either incorrectly interpreted by the system, or the system simply does not understand the question at all. This requires the user to follow-up with additional voice commands, clarifications, etc.

Other devices provide information about non-verbal (i.e., non-speech) inputs, but do not allow the user to generate and ask questions about the non-verbal inputs.

For example, U.S. Patent Application Publication No. 2012/0124461 describes a technique for annotating street level images with contextual information overlaid on the images. Similarly, U.S. Patent Application Publication No. 2013/0346068 describes a system that tags a digital photograph with certain user-provided terms. However, this type of art is limited to auto-populating an image with predefined information, without regard to a specific question that the use may have.

Thus, the prior art, either singularly or in combination, fails to provide a system that allows a user to ask a question, and then to augment that question using a non-verbal input that clarifies the question. That is, the prior art does not provide a system that allows a user to present user-generated questions to a device about non-verbal inputs such as visual images, scents, sounds, etc. The present invention provides one or more solutions to this long-felt need.

SUMMARY

In an embodiment of the present disclosure, an electronic device comprises a microphone for receiving an oral request for information about an unspecified object. A sensor receives augmentation information about the unspecified object. Combination logic combines information from the oral request with the augmentation information into a combined format information request. Information retrieval logic then retrieves an answer to the combined format information request.

In an embodiment of the present disclosure, the sensor in the electronic device is a chemical sensor, which is able to "smell" the object about which a question is asked by the user.

In an embodiment of the present disclosure, the sensor in the electronic device is a camera that captures a video image, and the unspecified object is an object that does not appear in the video image. The electronic device accesses a metadata retrieving logic to retrieve metadata from the video image captured by the camera that describes the video image. Correlation logic correlates information from the metadata to identify information about the unspecified object to generate an answer to the combined format request.

In an embodiment of the present disclosure, a method for augmenting an information request comprises receiving, by an information server, a request for information about an object. The request for information is from an electronic device, and is in a first format. The information server receives augmentation information about the object. The augmentation information is generated by the electronic device, and is in a second format that is different from the first format. The information server generates a response to the request for information based on the augmentation information.

In an embodiment of the present disclosure, the first format is for speech recognition, and the second format is for a photograph. The object about which information is requested is shown in the photograph. The information server retrieves embedded information in the photograph about the object shown in the photograph. The information server locates additional information about the object in the photograph based on the embedded information.

In an embodiment of the present disclosure, the request for information is generated by a specific user. The method further comprises associating the request for information with a user profile for the specific user, and tailoring the response to the request for information based on the user profile.

In an embodiment of the present disclosure, the information server receives a physical gesture of a user, and utilizes the physical gesture as the augmentation information about the object.

In an embodiment of the present disclosure, a computer program product augments an information request. The computer program product comprises a computer readable storage medium having program code embodied therewith, wherein the computer readable storage medium is not a transitory signal per se, and wherein the program code is readable and executable by a processor to perform a method comprising: receiving a request for information about an object, wherein the request for information is from an electronic device, and wherein the request for information is in a first format; receiving augmentation information about the object, wherein the augmentation information is generated by the electronic device, and wherein the augmentation information is in a second format that is different from the first format; and generating a response to the request for information based on the augmentation information.

The presently disclosed system thus provides a technological advantage over the prior art, in that it improves the efficiency and accuracy of an information request. More specifically, without the teachings of the present disclosure, many, if not most, oral questions would be meaningless, and therefore unanswerable by an intelligent assistant device.

DETAILED DESCRIPTION

Figure 1:
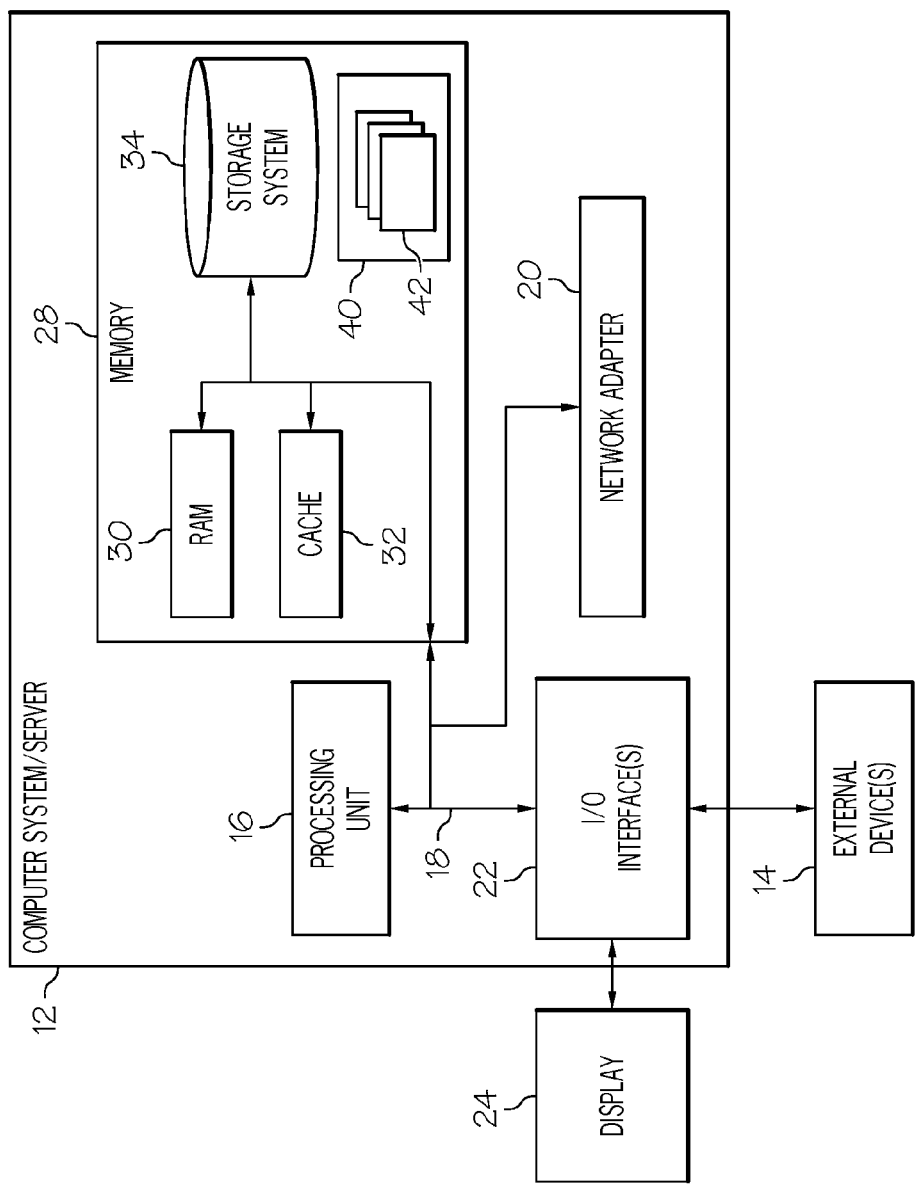
FIG. 1 depicts a cloud computing node according to an embodiment of the present disclosure.

The present invention may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that in one or more embodiments, the present invention is capable of being implemented in a cloud computing environment.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via I/O interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

In one or more embodiments of the present disclosure, external devices 14 utilize the architecture of the computer system/server 12 shown in FIG. 1. Similarly, the architecture of computer system/server 10 can be implemented in the electronic device 402 and/or the information cloud server 404 shown in FIG. 4.

Figure 2:
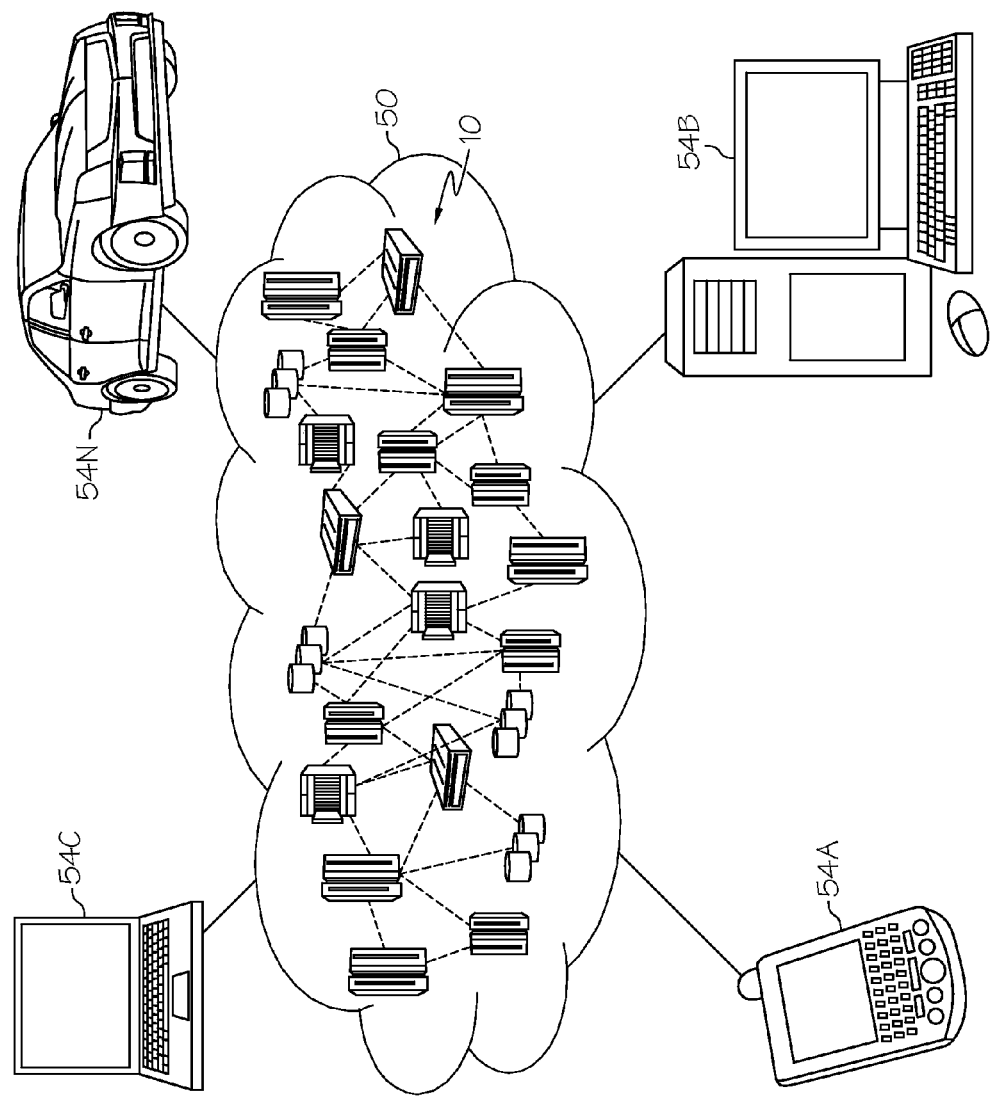
FIG. 2 depicts a cloud computing environment according to an embodiment of the present disclosure.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
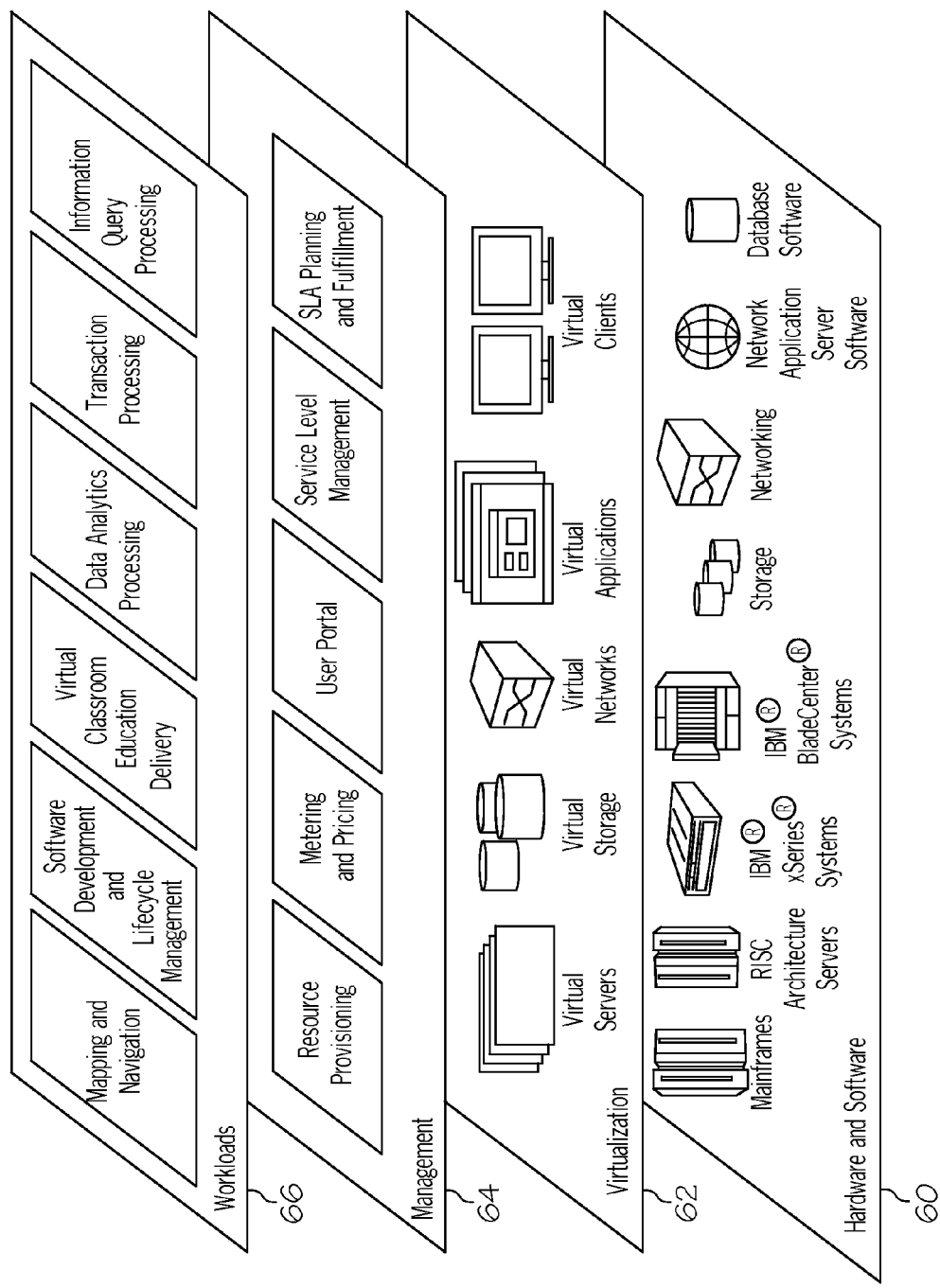
FIG. 3 depicts abstraction model layers according to an embodiment of the present disclosure.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide)

Virtualization layer 62 provides an abstraction layer from which the following examples of virtual entities may be provided: virtual servers; virtual storage; virtual networks, including virtual private networks; virtual applications and operating systems; and virtual clients.

In one example, management layer 64 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 66 provides examples of functionality for which the cloud computing environment may be utilized. Examples of workloads and functions which may be provided from this layer include: mapping and navigation; software development and lifecycle management; virtual classroom education delivery; data analytics processing; transaction processing; and handling information queries from electronic devices, as described herein, and as represented by the "Information Query Processing" found in workloads layer 66.

Figure 4:
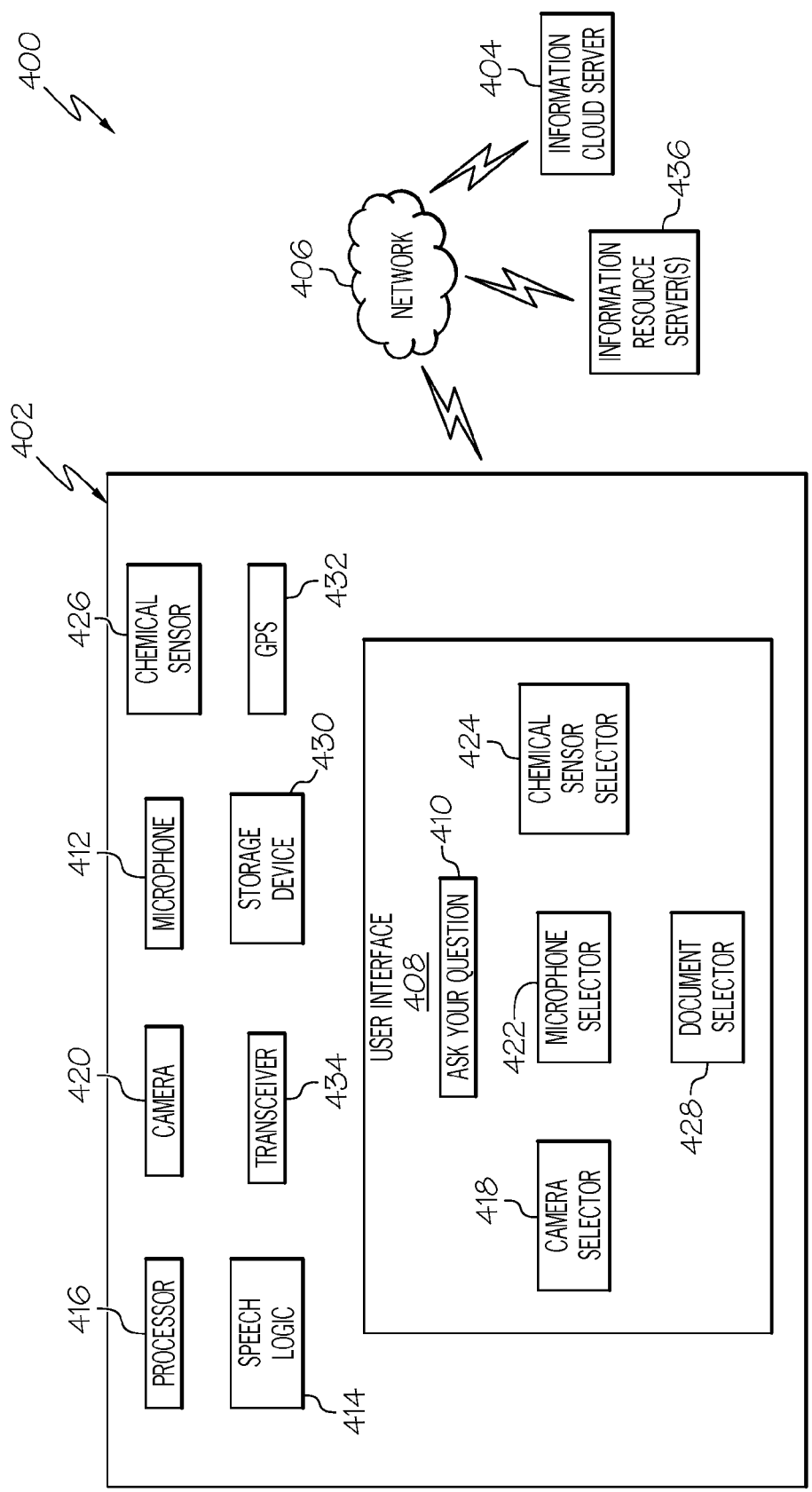
FIG. 4 illustrates an exemplary system in which the present invention may be utilized.

With reference now to FIG. 4, an exemplary system 400 depicts the technical characteristics and/or interoperability of various new and novel technical features not found in the prior art, and in which the present invention may be utilized. More specifically, the elements depicted in FIG. 4 and further described with respect to operations depicted in FIG. 5 solve the problem of a query logic being unable to clearly and efficiently identify the nature and scope of a user-generated information query. The present disclosure solves this problem thought the use of augmentation sensors (visual, sound, chemical, etc.) that clarify the nature of the subject of the query.

An electronic device 402, such as a smart phone, a personal digital assistant, a tablet computer, etc., is able to communicate with an information cloud server 404 via a network 406, which may be wired (e.g., the Internet), wireless (e.g., a Wi-Fi system), and/or a combination of both.

The electronic device 402 includes a user interface 408, which may prompt a user to "Ask your question", as shown in an "Ask your question" button 410. "Ask your question" button 410 may become highlighted when the user presses the "Ask your question" button 410 (which may be a mechanical button or a touch-sensitive area of the user interface 408), thus indicating that speech logic 414 has been enabled to receive the user's question via a microphone 412. The speech logic 414 converts the user's question into a digitized format, which can be processed locally by processor 416 and/or remotely by information cloud server 404.

In order to better understand the user's question, additional information is provided to the processor 416 and/or information cloud server 404 as "augmentation information". This augmentation information may be in the form of a photograph, a video, a sound, a chemical signature, a reference to a document, a reference to a graphic file, etc.

In an embodiment of the present disclosure, the user's question (i.e., oral request for information) is initially about an unspecified object. For example, the question may be "What kind of flower is this?" Using only the verbal question, the system is unable to "know" what "flower" the user is asking about, and thus the "flower" in question is unspecified (i.e., is an "unspecified object"). In accordance with one or more embodiments of the present invention, a sensor on the electronic device 402 provides augmentation information about the unspecified object.

In an embodiment of the present disclosure, the sensor that is used to provide this augmentation information is a camera 420, which creates a photograph (i.e., a still photograph) and/or a video (i.e., a visual recording of a moving image). Camera 420 is selected by the user pressing camera selector button 418, which activates the camera 420 on the electronic device 402. After taking a photograph/video of the flower with the camera 420, the system now has augmentation information about the query. That is, when the user asks "What type of flower is this?", the processor 416 and/or information cloud server 404 use combination logic (e.g., part of processor 416) to combine information from the oral question ("What type of flower is this?") with the augmentation information provided by the photograph of the flower to create a combined format information request. Using this combination of information, information retrieval logic (e.g., processor 416) is now able to retrieve an answer to the combined format information request (e.g., from the storage device 430). Thus, data query logic (e.g., part of the "Information Query Processing" shown in workloads 66 in FIG. 3) is provided with both the oral/verbal question as well as the visual information from the photograph/video. This allows the data query logic to both "hear" the question and "see" the subject of the question.

In an embodiment of the present disclosure, the processor 416 and/or information cloud server 404 uses image recognition software to identify the object (e.g., the "flower") in the photograph. That is, the processor 416 and/or information cloud server 404 generate a digital representation of the flower, including its shape, color, number of petals, etc., and compare that digital representation with a database of digital information about flowers, in order to identify the flower as a rose. This information (i.e., flower type is a "rose") is combined with the question ("What type of flower is this?") to create the combined format information request. In this example, the system simply returns the answer "This flower is a rose" from the augmentation information.

In an embodiment of the present disclosure, the combined format information request enables the data query logic to examine relevant databases. For example, assume still that the query from the user is "What type of flower is this?" and the augmentation information created by the photograph from camera 420 reveals that the flower is a "rose". The data query logic can then use these key words (i.e., "rose", "flower") to examine other databases about the "rose", including where it grows, what it needs to flourish (water, food, sunlight, etc.), its Latin binomial name, etc. The speech logic 414 can then prompt the user with an offer to provide additional information from the examined database(s). In an embodiment, this offer is based on a profile of the user stored in a database such as that found (not shown) in storage device 430 in FIG. 4. For example, if storage device 430 contains a record that the user is a gardener, then gardening recommendations may be offered, while if storage device 430 contains a record that the user is a botany student, then the Latin binomial name may be offered. Similarly, if the user is a chemist (according to his/her stored profile), then a description of which perfumes are made from this type of rose may be offered.

In an embodiment of the present disclosure, the data query logic (e.g., processor 416 and/or information cloud server 404) may provide information about the user himself/herself. For example, assume that the storage device 430 contains an entry about the user of the electronic device 402 indicating that this user has had knee surgery. Assume further that the user takes a picture of his/her knee with camera 420, and then asks the question "Is my knee okay?" Processor 416 will then compare the current picture of the knee with a previous picture of the knee (stored in a profile for this user in storage device 430). If the knee looks like it did immediately after a time in which the user previously injured his/her knee, then the data query logic may return the answer "Your knee appears to have been reinjured". However, if the visual image of the knee appears "normal" when compared to other photographs of the user's knee (or other patients' knees) that are uninjured, then the data query logic would return the answer "Your knee looks fine".

Similarly, a user may ask the data query logic about food choices for that particular user. For example, assume that a user of the electronic device 402 is on a low sodium diet, and is standing before a food buffet. The user may take a photograph of the food buffet with the camera 420, and send that photograph to the data query logic with the question "What should I eat?" The data query logic will use visual recognition logic to identify the different types of food; query a database of nutrition facts about the identified types of food; and return a response instructing the user to select certain food from the photograph that is low in salt.

While clicking the camera selector button 418 enables capturing an image, in an embodiment of the present invention engaging the camera selector button 418 allows a live-stream of data to be sent to the data query logic, along with the user's verbal question. Similarly, the camera 420 may always be active in an embodiment, such that the user need not even engage the camera selector button 418.

Thus, as described above, one or more embodiments of the present disclosure allow data query logic associated with the electronic device 402 to not only "hear" the question (by the user clicking the "Ask your question" button 410), but to also "see" what the user is asking about. While the embodiment described above has been presented as using a photograph, the same process can be utilized on a video stream.

In an embodiment of the present disclosure, the electronic device 402 is able to not only "hear" the question (by the user clicking the "Ask your question" button 410), but to also "hear" what the user is asking about, by the user pressing the microphone selector button 422, which activates the microphone 412 on the electronic device 402. For example, assume that the user has verbally asked the question "What type of bird is that?" Using only the verbal question, the system is unable to "know" what "bird" the user is asking about. However, the microphone 412 (an audio/aural sensor) on the electronic device 402 provides augmentation about the unspecified object (the "bird") according to its song. In an embodiment of the present disclosure, the processor 416 and/or information cloud server 404 use sound pattern recognition software to identify the "bird" heard in the sound capture as a "meadowlark". That is, the processor 416 and/or information cloud server 404 generate a digital representation of the bird's song, including its pitch, pattern, timbre, etc., and compare that sound signature with a database of digital information about birdsongs, in order to identify the bird as a meadowlark. This information (i.e., bird type is a "meadowlark") is combined with the question ("What type of bird is that?") to return an answer "This bird is a meadowlark." Thus, the data query logic (e.g., part of the "Information Query Processing" shown in workloads 66 in FIG. 3) is provided with both the oral/verbal question as well as the augmentation information from the sound recording/capture. This allows the data query logic to both "hear" the question and to "hear" the subject of the question. In one example, the system simply returns the answer "This bird is a meadowlark" from the augmentation information found in the sound recording.

In an embodiment of the present disclosure, the combined format information request enables the data query logic to examine relevant databases based on what the data query logic "heard" from the object being inquired about. For example, assuming still that the query from the user is "What type of bird is this?" and the augmentation information created by the sound recording from microphone 412 reveals that the bird is a meadowlark. The data query logic can then pursue other databases about the "meadowlark", including where it lives, if it is a game bird, its Latin binomial name, etc. The speech logic 414 can then prompt the user with an offer to provide such additional information. In an embodiment, this offer is based on a profile of the user. For example, if storage device 430 contains a record that the user is a hunter, then the data query logic may offer (or automatically reveal) to the hunter that a meadowlark is not a game bird (and thus is not to be shot). Similarly, if storage device 430 contains a record that the user is a bird watcher (ornithologist), then the Latin binomial name may be offered by the data query logic to the user.

In an embodiment of the present disclosure, once an object is identified by its image and/or sound, suggested actions may be presented to the user. For example, assume that a user of the electronic device 402 has taken an audio/visual recording of a motor, and asked the question "Is this motor running properly?" Image recognition software will identify the type of motor from the video component of the recording. Sound pattern recognition will identify any anomaly in the motor by comparing the audio component of the recording with a digital database of normal and/or abnormal sounds for this motor. That is, the digitized sound pattern from the audio portion of the recording is used to identify any problem with the motor by comparing the digitized sound pattern with known sound signatures (normal and abnormal) for this motor. The system can then access a database of solutions for the identified problem, and present these solution(s) to the user. For example, if the sound signature for this motor suggests that a main bearing is going out, then the system may offer directions for replacing the main bearing, which part number is associated with the needed main bearing, an estimate of how long the job will take (and thus how long the system that uses the motor will be out of operation), etc.

In an embodiment of the present disclosure, the electronic device 402 is able to not only "hear" the question (by the user clicking the "Ask your question" button 410), but to also "smell" what the user is asking about, by the user pressing the chemical sensor selector button 424, which activates the chemical sensor 426 on the electronic device 402. For example, assume that the user is standing next to a food vendor cart and asks the question "What type of food is this?" Using only the verbal question, the system is unable to "know" what "food" the user is asking about. However, the chemical sensor 426 on the electronic device 402 provides augmentation about the unspecified object according to its aroma. In an embodiment of the present disclosure, the processor 416 and/or information cloud server 404 uses chemical pattern recognition software to identify the "smell" received by the chemical sensor capture as being a "hotdog". That is, the processor 416 and/or information cloud server 404 generate a digital file that describes the hotdog's aroma, generated by one or more sensors within the chemical sensor 426 that can detect the chemical signature of beef, salt, certain spices, etc., and compares that chemical signature with a database of digital information about food, in order to identify the food as a hotdog. This information (i.e., food type is a "hotdog") is combined with the question ("What type of food is this?") to return an answer "This food is a hotdog." Thus, the data query logic (e.g., part of the "Information Query Processing" shown in workloads 66 in FIG. 3) is provided with both the oral/verbal question as well as the augmentation information from the chemical signature. This allows the data query logic to both "hear" the question and "smell" the subject of the question. In this example, the system simply returns the answer "This food is a hotdog" from the augmentation information found in the sound recording. In additional embodiments, this information can then be used, based on the user's profile, etc., to provide suggestions as to whether this user should eat the hotdog at all (based on his/her medical history), which hotdog offered by this vendor is highest rated, if there is a higher-rated hotdog vendor nearby, etc.

In an embodiment of the present disclosure and as shown in FIG. 4, the electronic device 402 includes a transceiver 434, which is able to send and receive electronic messages, either wirelessly or over a hard wire. Transceiver 434 is able to transmit the combined format request (discussed above) to an information server.

In an embodiment of the present disclosure, the information server is a local device on the electronic device 402, such as the processor 416. Thus, any queries are handled locally by the electronic device 402.

In an embodiment of the present disclosure, the information server is a remote device, such as the information cloud server 404, which is able to handle information requests from multiple electronic devices.

In an embodiment of the present disclosure, the information server is a combination of a local device (e.g., processor 416) and a remote device (e.g., information cloud server 404).

In one or more embodiments of the present disclosure, the electronic device 402 includes a positioning logic, such as the depicted global positioning system (GPS) 432. GPS 432 utilizes a series of geosynchronous satellites to mark the position of the electronic device 402 at any point in time. Other positioning logic (not depicted) may be in the form of triangulation systems (which use signals from transmitters within a room to position a device), Doppler-shift systems (which use the time it takes for a signal to go from a positioning transmitter/receiver at a known location to the electronic device 402 and back to the positioning transmitter/receiver), etc. Thus, metadata about a real-time location of the electronic device 402 when a question is asked and/or when augmentation information (e.g., a photograph, a sound recording, a chemical reading, etc.) is generated is created by the GPS 432.

In an embodiment of the present invention, the data query logic (e.g., processor 416 and/or information cloud server 404) may not have enough information locally stored to answer questions about the object being viewed/smelled/etc. and queried about. In this scenario, the data query logic can access information resource server(s) 436, such as systems that provide access to information resources such as websites, databases, etc. Such information resources are selectively accessed/retrieved using a web crawler, a search engine, a database search logic, etc., in order to access particular information. For example, assume that the user has asked "What perfumes are made from this flower?", and that the data query logic has received both the question as well as a photo of the flower in question, and has determined that the flower is a rose.

The data query logic will then crawl/query information resources provided by the information resource server(s) 436, in order to identify which perfumes (including product names, manufacturers, etc.) use rose essence in their formulation.

Figure 5:
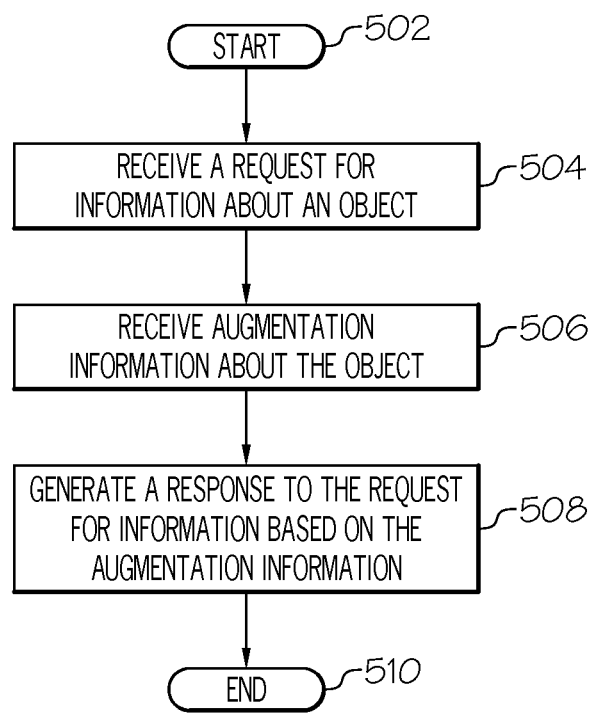
FIG. 5 is a high level flow-chart of one or more operations performed by one or more processors or other hardware devices to respond to a user-generated request for information from an electronic device.

With reference now to FIG. 5, a high level flow-chart of one or more operations performed by one or more processors or other hardware devices to respond to a user-generated request for information from an electronic device through augmentation of the information request is presented.

After initiator block 502, an information server receives a request for information about an object (block 504). As described in FIG. 4, the information server may be local (e.g., processor 416), remote (e.g., information cloud server 404), and/or a combination thereof. The request for information is from an electronic device (e.g., electronic device 402 in FIG. 4). The request for information is in a first format, such as that used in speech conversion/digitization by speech logic 414 in FIG. 4. For example, the request for information may be from a user "asking" the electronic device 402 a question about a particular subject/object. However, it is initially unclear to the information server what the user is asking about.

Therefore, in block 506, the information server receives augmentation information about the object. This augmentation information is generated by the electronic device, and is in a second format that is different from the first format. For example, the first format may be that used by a speech digitizer to convert a user's oral question into a digitized format. The second format may be that used by a photograph, a video file, a chemical signature, a text document, a graphic file, etc.

As described in block 508, the information server is then able to generate a response to the request for information based on the augmentation information. That is and as described above, subjects such as "flower" and "motor" and "knee" are now described with better specificity by an accompanying photo/sound recording/chemical signature/etc., thus enabling the information server to better respond to the query.

Thus, in an embodiment of the present disclosure, the first format is for speech recognition, and the second format is for a video file that is generated by a camera on the electronic device.

Thus, in an embodiment of the present disclosure, the first format is for speech recognition, and the second format is for an audio file that is generated by a microphone on the electronic device.

Thus, in an embodiment of the present disclosure, the first format is for speech recognition, and the second format is for a chemical signature that is generated by a chemical sensor on the electronic device.

In an embodiment of the present disclosure, the first format is for speech recognition, and the second format is for a text document that is received from the electronic device. For example, assume that a user has pressed the document selector button 428 in FIG. 4. This causes the processor 416 and/or the information cloud server 404 to retrieve a text document, which has either been previously stored (e.g., in the storage device 430) or is currently being created by the user drawing on the user interface 408 (e.g., using his/her fingertip on a touch sensitive portion of the screen devoted to receiving free-form text that is converted into ASCII characters). The user can then ask a question such as "What is this text document about?", "Is this document appropriate for sending to a customer?", etc. Similarly, the query may be "What does this text document mean?" The data query logic can then compare text in (or metatags from) the selected text document with a database that describes documents, in order to answer such questions.

In an embodiment of the present disclosure, the first format is for speech recognition, and the second format is for a graph document that is stored on the electronic device. For example, assume that the user has pressed the document selector button 428 in FIG. 4. This causes the processor 416 and/or the information cloud server 404 to retrieve a graphics file, which has either been previously stored (e.g., in the storage device 430) or is currently being created by the user drawing on the user interface 408 (e.g., using his/her fingertip on a touch sensitive portion of the screen devoted to receiving free-form text that is converted into ASCII characters). The user can then ask a question such as "What is this figure depicting?", "What does this graph tell us about current sales figures?", etc. The data query logic can then extract information from the figure/graph (including metatags) with a database that describes other graphs/figures, in order to answer such questions.

In an embodiment of the present disclosure, the first format is for speech recognition, the second format is for a photograph, and the object being asked about is shown in the photograph. In this embodiment, the information server retrieves embedded information in the photograph about the object shown in the photograph, and the embedded information describes the object shown in the photograph. The information server then locates additional information about the object in the photograph based on the embedded information, such that the additional information surpasses the embedded information. That is, as described above, embedded information in the photograph such as metatags, can be used to retrieve additional information about the object shown in the photograph. For example, assume that the photograph was taken by the camera 420 shown in FIG. 4, and that GPS 432 or similar positioning logic has placed a metatag on the photograph showing the time, date, and location at which the photograph was taken. Assume further that the photograph was a "selfie" of a user and friend, and the question (posed immediately or at a later time/date) is "What is the birthdate of my friend on the right side of the picture?" By correlating the metadata from the photograph (e.g., a tag that identifies the friend) with a database of information (e.g., from a social media website that the user is authorized to access), then the birthdate of the friend can be derived by the data query logic (e.g., the "Information Query Processing" shown in workloads 66 in FIG. 3).

In an embodiment of the present disclosure, the first format is for speech recognition, the second format is for a photograph, and the object being asked about is not shown in the photograph. In this embodiment, the information server utilizes embedded information in the photograph to retrieve additional information about the object not shown in the photograph, wherein the additional information surpasses the embedded information. For example, assume that the photograph was taken by the camera 420 shown in FIG. 4, and that GPS 432 or similar positioning logic has placed a metatag on the photograph showing the time, date, and location at which the photograph was taken. Assume further that the photograph was a "selfie" of a user and friend at a music festival, and the question (posed immediately or at a later time/date) is "What band was playing when this picture was taken?", even though the band being asked about is not in the photograph. By correlating the metadata from the photograph with a schedule of bands (and even songs from a playlist) for any particular time, the name of the band (and/or the song that was being played) at the time of the photograph can be derived by the data query logic (e.g., the "Information Query Processing" shown in workloads 66 in FIG. 3).

In an embodiment of the present disclosure, the request for information is generated by a specific user, and the method further comprises associating the request for information with a user profile for the specific user; and tailoring the response to the request for information based on the user profile. For example and as described above, information about a bird will be different if the user is a hunter or an ornithologist.

In an embodiment of the present disclosure, the information server receives a physical gesture of a user, and then utilizes the physical gesture as additional augmentation information about the object. For example, assume that the user of the electronic device 402 is taking a video and/or photograph of a group of cars. The user may be interested in the make and model of a particular car (or in the case of a racecar on a track, the driver of a particular racecar) in the video/photograph. In order to specify which car is the subject of the user's question "What kind of car is that?" or "Who is the driver of that racecar?", the user may include a hand gesture within the photograph/video, such as a finger point, a circle created by the thumb and forefinger, etc., in order to specify which car is of interest.

As described herein and in one or more embodiments, the present disclosure enables a user to request a search with voice recognition software, while providing more details about the search request through use of non-voice inputs. The present disclosure enables an intelligent automated assistant with voice recognition capability to analyze drawings, photos, sounds, chemical signatures, etc. in order to better understand the nature of the search request. As described herein, a user can, in real time, point a mobile device (e.g., a smart phone) at an object to discover more about that object's characteristics (e.g., visual, tonal, scent, etc.). The present disclosure thus presents a technological improvement over the prior art that has heretofore been unavailable and/or known to those skilled in the art.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof The corresponding structures, materials, acts, and equivalents of all means or step plus function elements in the claims below are intended to include any structure, material, or act for performing the function in combination with other claimed elements as specifically claimed. The description of various embodiments of the present disclosure has been presented for purposes of illustration and description, but is not intended to be exhaustive or limited to the present invention in the form disclosed. Many modifications and variations will be apparent to those of ordinary skill in the art without departing from the scope and spirit of the present disclosure. The embodiment was chosen and described in order to best explain the principles of the present disclosure and the practical application, and to enable others of ordinary skill in the art to understand the present invention for various embodiments with various modifications as are suited to the particular use contemplated.

Any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the present disclosure of the present application in detail and by reference to illustrative embodiments thereof, it will be apparent that modifications and variations are possible without departing from the scope of the present disclosure defined in the appended claims.

What is claimed is:

1. An electronic device comprising:
   a microphone for receiving an oral request for information about an unspecified object;
   a camera for receiving augmentation information about the unspecified object, wherein the augmentation information is in a video file generated by the camera;
   combination logic for combining information from the oral request with the augmentation information into a combined format information request;
   information retrieval logic for retrieving an answer to the combined format information request;
   a metadata retrieving logic, wherein the unspecified object is an object that is represented by the video file, wherein the metadata retrieving logic retrieves metadata from the video file that describes the object represented by the video file; and
   correlation logic that correlates information from the metadata to identify information about the unspecified object to generate an answer to the combined format information request.

2. The electronic device of claim 1, further comprising:
   a transmitter for transmitting the combined format information request to an information server.

3. A method for augmenting an information request, the method comprising:
   receiving, by an information server, a request for information about an object, wherein the object is shown in a photograph, wherein the request for information is from an electronic device, and wherein the request for information is in a first format, wherein the first format is for speech recognition;
   receiving, by the information server, augmentation information about the object, wherein the augmentation information is generated by the electronic device, wherein the augmentation information is in a second format that is different from the first format, and wherein the second format is for the photograph;
   generating, by the information server, a response to the request for information based on the augmentation information;
   retrieving, by the information server, embedded information in the photograph about the object shown in the photograph, wherein the embedded information describes the object shown in the photograph; and
   locating, by the information server, additional information about the object in the photograph based on the embedded information, wherein the additional information surpasses the embedded information.

4. The method of claim 3, wherein the object is not shown in the photograph, and wherein the method further comprises:
   utilizing, by the information server, embedded information in the photograph to retrieve additional information about the object not shown in the photograph, wherein the additional information surpasses the embedded information.

5. The method of claim 3, wherein the request for information is generated by a specific user, and wherein the method further comprises:
   associating the request for information with a user profile for the specific user; and
   tailoring the response to the request for information based on the user profile.

6. The method of claim 3, further comprising:
   receiving, by the information server, a physical gesture of a user; and
   utilizing, by the information server, the physical gesture as additional augmentation information about the object.

7. A computer program product for augmenting an information request, the computer program product comprising a computer readable storage medium having program code embodied therewith, wherein the computer readable storage medium is not a transitory signal per se, and wherein the program code is readable and executable by a processor to perform a method comprising:
   receiving a request for information about an object, wherein the request for information is from an electronic device, and wherein the request for information is in a first format, wherein the first format is for speech recognition;
   receiving augmentation information about the object, wherein the augmentation information is generated by the electronic device, and wherein the augmentation information is in a second format that is different from the first format, wherein the second format is for a video file, and wherein the object is not represented by the video file;
   generating a response to the request for information based on the augmentation information; and
   utilizing embedded information in the video file to retrieve additional information about the object not represented by the video file, wherein the additional information surpasses the embedded information.

8. The computer program product of claim 7, wherein the object is a photograph that is represented by the video file, and wherein the method further comprises:
   retrieving embedded information about the object shown in the photograph, wherein the embedded information describes the object shown in the photograph; and
   locating additional information about the object in the photograph based on the embedded information, wherein the additional information surpasses the embedded information.

* * * * *